US007824861B2

(12) United States Patent
Chow

(10) Patent No.: US 7,824,861 B2
(45) Date of Patent: Nov. 2, 2010

(54) METHOD FOR QUANTITATIVE ANALYSIS OF TRANSCRIPTS WITH NUCLEOTIDE POLYMORPHISM AT SPECIFIC SITE

(75) Inventor: Wei-Yuan Chow, Hsinchu (TW)

(73) Assignee: National Tsing Hua University, Hsinchu (TW)

( * ) Notice: Subject to any disclaimer, the term of this patent is extended or adjusted under 35 U.S.C. 154(b) by 136 days.

(21) Appl. No.: 12/171,239

(22) Filed: Jul. 10, 2008

(65) Prior Publication Data

US 2010/0009350 A1    Jan. 14, 2010

(51) Int. Cl.
*C12Q 1/68* (2006.01)
*C12P 19/34* (2006.01)
*C07H 21/02* (2006.01)
*C07H 21/04* (2006.01)

(52) U.S. Cl. .................. 435/6; 435/91.2; 536/23.1; 536/24.3

(58) Field of Classification Search .............. 435/6, 435/91.2; 536/23.1, 24.3
See application file for complete search history.

(56) References Cited

U.S. PATENT DOCUMENTS

| 5,804,383 A * | 9/1998 | Gruenert et al. ................ 435/6 |
| 2008/0075662 A1 * | 3/2008 | Madjar et al. ................. 435/6 |
| 2010/0009350 A1 * | 1/2010 | Chow ............................ 435/6 |

OTHER PUBLICATIONS

Chen et al., A real-time PCR method for the quantitative analysis of RNA editing at specific sites. Analytical Biochemistry 375 (1): 46-52 (Jan. 2008).*
Giuletti et al, An overview of real-time quantitative PCR: applications to quantify cytokine gene expression. Methods 25 : 386-401 (2001).*
Keegan et al., Tuning of RNA editing by ADAR is required in Drosophila. EMBO J. 24 :2183-2193 (2005).*
Wu et al. Determination of relative abundance of splicing variants of Oreochromis glutamate receptors by quantitative reverse-transcriptase PCR. FEBS Letters 390 : 157-160 (1996).*
Schiffer et al., A quantitative method to detect RNA editing events. Analytical Biochemistry 276 : 257-260 (1999).*
Brenda L. Bass; RNA Editing by Adenosine Deaminases That Act on RNA; Annu. Rev. Biochem.; 2002; pp.817-846; vol. 71; Annual Reviews.
Stefan Mass et al.; A-toI RNA Editing and Human Disease; RNA Biology Review; Jan./Feb. Mar. 2006; pp. 1-9; vol. 3, No. 1; Landes Bioscience.
Hans H. Schiffer et al.; A Quantitative Method to Detect RNA Editing Events; Analytical Biochemistry; 1999; pp. 257-260; vol. 276; Notes and Tips; Academic Press.
Peter H. Seeburg et al.; RNA editing of brain glutamate receptor channels: mechanism and physiology; Brain Research Review; 1998; pp. 217-229; vol. 26; Elsevier.
Joseph E. Wedekind et al.; Messenger RNA editing in mammals: new members of the APOBEC family seeking roles in the family business; TRENDS in Genetics; Apr. 2003; pp. 207-216; vol. 19, No. 4; Review; Elsevier.
Susan M. Rueter et al.; Regulation of alternative splicing by RNA editing; letters to nature; May 6, 1999; pp. 75-80; vol. 399; Nature; Macmillan Magazines Ltd.
Yukio Kawahara, et al.; Redirection of Silencing Targes by Adenosine-to-Inosine Editing of miRNAs; Science; Feb. 23, 2007; pp. 1137-1140; vol. 315; Science.
Weidong Yang, et al.; Modulation of microRNA processing and expression through RNA editing by ADAR deaminases; nature structure & molecular biology; Jan. 2006; pp. 13-21; vol. 13, No. 1; Articles; Nature.
David Sidransky, et al.; Identification of ras Oncogene Mutations in the Stool of Patients with Curable Colorectal Tumors; Science; Apr. 3, 1992; pp. 101-105; vol. 256; Science; Jstor.
Wei-Hsiang Lin, et al.; Embryonic expression of zebrafish AMPA receptor genes . . .; Brain Research; 2006; pp. 46-54; vol. 1110; ScienceDirect; Elsevier.
Scott M. Blecher, et al.; Characterization of RNA editing of the glutamate-receptor subunits GluR5 and GluR6 in granule cells during cerebellar development; Molecular Brain Research; 1997; pp. 130-138; vol. 52; Elsevier.
Liam P Keegan, et al.; Tuning of RNA editing by ADAR is required in Drosophila; The EMBO Journal; 2005; pp. 2183-2193; vol. 24; European Molecular Biology Organization.

* cited by examiner

*Primary Examiner*—Ethan Whisenant
(74) *Attorney, Agent, or Firm*—WPAT, P.C.; Anthony King

(57) ABSTRACT

The present invention provides a quantitative method for assaying the expression ratio between alleles differed by a single nucleotide polymorphism.

9 Claims, 5 Drawing Sheets

A. Steps of qPCR analysis

B. Locations of the qPCR primers

METHOD FOR QUANTITATIVE ANALYSIS OF TRANSCRIPTS WITH NUCLEOTIDE POLYMORPHISM AT SPECIFIC SITE

FIELD OF THE INVENTION

This invention relates to a quantitative method for assaying the expression ratio between alleles differed by a single nucleotide polymorphism.

DESCRIPTION OF PRIOR ART

Germ-line and somatic mutations are responsible for a plethora of human diseases. Specific nucleic acid variations, such as mutations, insertions, deletions and other alterations can serve as valuable markers for a variety of diseases, including certain types of cancer. For example, mutations in the BRCA genes have been proposed as indications for breast cancer, and mutations in the p53 cell cycle regulator gene have been associated with numerous cancers, especially colorectal cancer. It has been suggested that specific variations might be a basis for molecular screening assays for the early stages of certain types of cancer. See, e.g., Sidransky, et al., Science, 1992, 256: 102-105. Therefore, in an effort to detect whether certain variations have occurred and further ascertain whether a person is at risk for developing a disease associated with these variations, molecular screening assays have been developed.

RNA editing is a site-specific modification of RNA molecules by nucleotide insertion/deletion, substitution and modification. The RNA editing by selective deamination of adenosine (A-to-I) and cytosine (C-to-U) results in sequence discrepancies between metazoan nuclear transcripts and genomic DNA (B. L. Bass, RNA editing by adenosine deaminases that act on RNA, Annu. Rev. Biochem. 71, 2002, 817-46; J. E. Wedekind, G. S. Dance, M. P. Sowden, and H. C. Smith, Messenger RNA editing in mammals: new members of the APOBEC family seeking roles in the family business, Trends Genet., 2003, 19: 207-16). Many protein-coding RNAs, such as those encoding neurotransmitter receptors, ion channels, the coat protein of hepatitis delta virus and adar2, one of the enzymes catalyzing A-to-I RNA editing, are modified at specific sites by the A-to-I editing (P. H. Seeburg, M. Higuchi, and R. Sprengel, RNA editing of brain glutamate receptor channels: mechanism and physiology, Brain Res. Brain Res. Rev., 1998, 26: 217-29; S. M., Rueter, T. R. Dawson, and R. B. Emeson, Regulation of alternative splicing by RNA editing, Nature, 1999, 399: 75-80). Since I is recognized as G, RNA editing of the aforementioned transcripts affects the splicing of pre-mRNAs and the translated sequences. A-to-I editing of RNA is most often incomplete, resulting in the coexistence of a heterogeneous pool of RNAs with A and I (G) variations at specific sites and in protein isoforms with distinct properties. A-to-I editing also modifies the noncoding regions and precursors of micro-RNA, affecting the biogenesis and activities of these RNAs (W. Yang, T. P. Chendrimada, Q. Wang, M. Higuchi, P. H. Seeburg, R. Shiekhattar, and K. Nishikura, Modulation of microRNA processing and expression through RNA editing by ADAR deaminases. Nat. Struct. Mol. Biol., 2006, 13: 13-21; Y. Kawahara, B. Zinshteyn, P. Sethupathy, H. Iizasa, A. G. Hatzigeorgiou, and K. Nishikura, Redirection of silencing targets by adenosine-to-inosine editing of miRNAs, Science, 2007, 315: 1137-40). Activity of RNA editing is under temporal and spatial regulations, and is altered under pathological conditions (S. Maas, Y. Kawahara, K. M. Tamburro, and K. Nishikura, A-to-I RNA Editing and Human Disease, RNA Biol., 2006, 3: 1-9).

Many methods have been developed to quantify the proportions of edited transcript in reverse transcript PCR amplicons. For example, sequence analysis and limited primer extension, in the presence of dideoxynucleotide, are widely used to quantitatively measure the RNA editing efficiency (H. H. Schiffer, and S. F. Heinemann, A quantitative method to detect RNA editing events, Anal. Biochem., 1999, 276: 257-60; L. P. Keegan, J. Brindle, A. Gallo, A. Leroy, R. A. Reenan, and M. A. O'Connell, Tuning of RNA editing by ADAR is required in *Drosophila*, EMBO J., 2005, 24: 2183-93). These methods, however, are laborious, costly and sometimes required cloning. Alternatively, restriction enzyme analysis is applied when RNA editing alters the recognition sequences of enzymes (S. M. Belcher, and J. R. Howe, Characterization of RNA editing of the glutamate-receptor subunits GluR5 and GluR6 in granule cells during cerebellar development, Brain Res. Mol. Brain Res, 1997, 52: 130-8). However, it can only detect RNA editing site consists of the recognition sequences of restriction enzymes. There are more methods for analyzing nucleic acids by detecting a difference of one or a few nucleotides in a given sequence such as ligase chain reaction (LCR), ligase detection reaction and PCR-mutant allele specific amplification (PCR-MASA) as described in the prior art of US Patent Pub. No. US 2008/0075662, and single strand conformation polymorphism.

Figure 1:
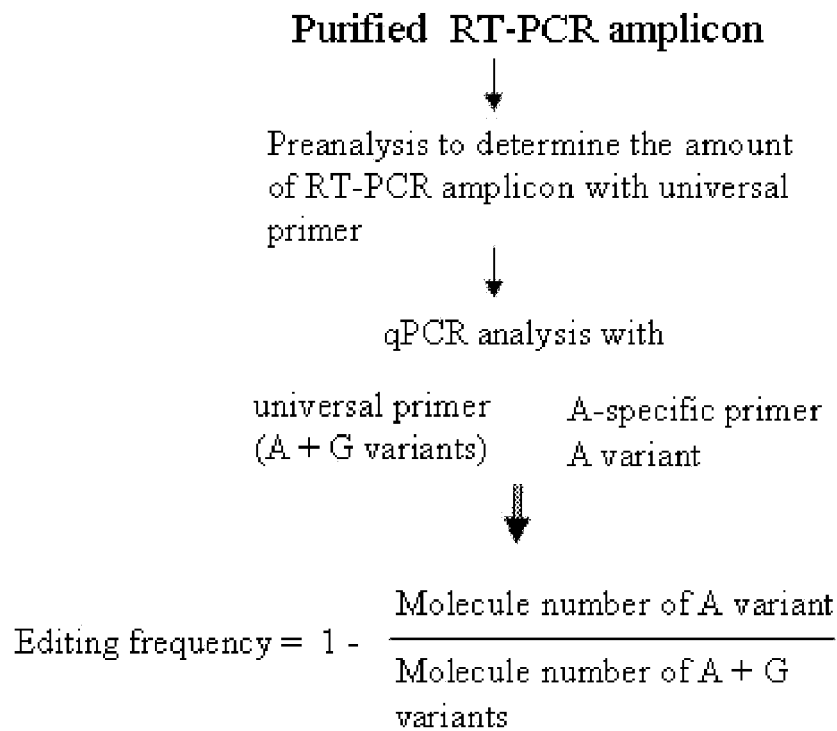
FIG. 1 illustrates schematic illustration of quantitative PCR analysis of RNA editing frequency. A. The steps involved in quantitative PCR analysis. B. The relative locations of PCR primers. Arrows depict the annealing sites of quantitative PCR (qPCR) primers.
Figure 1:
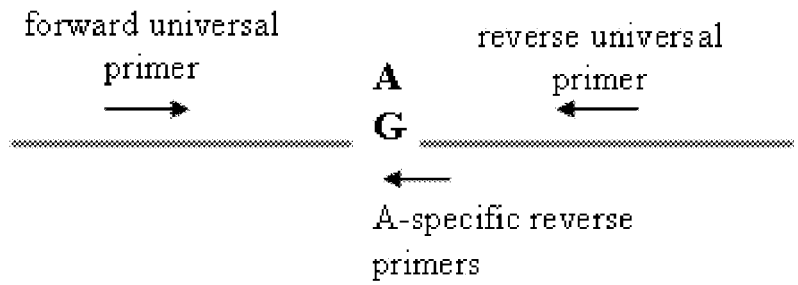

Asterisks indicate significant differences to the RNA editing levels at 24 hpf (P<0.05). (B) Representative chromatograms of sequence analysis.

SUMMARY OF THE INVENTION

The present invention provides a quantitative method for assaying the expression ratio between alleles differed by a single nucleotide polymorphism which comprises:
(a) designing an allele-specific primer, according to nucleotide sequence of one allele, which has, in 3' to 5' order, a 3'-hydroxyl allele-specific nucleotide, 3' perfect match nucleotides and 5' perfect match nucleotides; wherein the allele-specific nucleotide is derived from known single nucleotide polymorphic site;
(b) performing a polymerase chain reaction with an universal primer set which anneals to both alleles to obtain a total molecule number;
(c) performing the polymerase chain reaction with an allele-specific primer and one of the universal primers to obtain the molecule number of one allele; and
(d) calculating an expression frequency of one allele by molecular number of one allele/total molecular number.

The present invention further provides a quantitative method for assaying the expression ratio between alleles differed by a single nucleotide polymorphism which comprises:
(a) designing an allele-specific primer, according to nucleotide sequence of one species, which has, in 3' to 5' order, a 3'-hydroxyl allele-specific nucleotide, 3' perfect match nucleotides, at least one destabilizing mismatch nucleotide and 5' perfect match nucleotides, wherein the destabilizing mismatch nucleotide is selected from the group consisting of 3, 4, 5, 6 and 7 nucleotides upstream from the 3'-hydroxyl allele-specific nucleotide and is created by introducing transition or transversion substitution; and wherein the allele-specific nucleotide is derived from known single nucleotide polymorphic site;
(b) performing a polymerase chain reaction with an universal primer set which anneals to both alleles to obtain a total molecule number;
(c) performing the polymerase chain reaction with an allele-specific primer and one of the universal primers to obtain the molecule number of one allele; and
(d) calculating an expression frequency of one allele by molecular number of one allele/total molecular number.

DETAILED DESCRIPTION OF THE INVENTION

The term "allele" used herein includes variant nucleotide species and generally denotes any of one or more alternative form of a given gene; both (or all) alleles of a given gene are concerned with the same trait or characteristic but the product or function coded for by a particular allele differs, qualitatively and/or quantitatively, from that coded for by other alleles of that gene. Variants denote variations of nucleotide sequence among alleles, with or without known functional differences. It might also result in variants in nucleotide sequences.

The term "3' perfect match nucleotides" used herein means nucleotides of primer next to the 5' end of allele-specific nucleotide and perfectly match to the complimentary nucleotide sequence. The length of 3' perfect matches nucleotides ranges from 2 to 6 nucleotides.

The term "destabilizing mismatch nucleotide" used herein denotes primer contains one or more than one internal nucleotide substitutions resulting in a destabilization of the base pairing between primer and template.

The term "5' perfect match nucleotides" used herein means nucleotides next to the 5' end of destabilizing mismatch nucleotide or 5' end of the 3' perfect match nucleotides when destabilizing mismatch nucleotide do not present.

The term "RNA editing" used herein means a site-specific modification of RNA molecules by nucleotide insertion/deletion, substitution or modification, including the deamination of adenosines (A) to inosines or the deamination of cytosin (C) to uracil (U).

The present invention provides an easy and cost-effective method for quantifying unedited variants in mixtures of edited and unedited nucleotide variants by designing allele-specific PCR primers capable of differentially amplifying two alleles differed by a single nucleotide polymorphism without cloning, extensive purification of RT-PCR amplicons and using isotope.

Accordingly, the present invention provides a quantitative method for assaying the expression ratio between alleles differed by a single nucleotide polymorphism which comprises:
(a) designing an allele-specific primer, according to nucleotide sequence of one allele, which has, in 3' to 5' order, a 3'-hydroxyl allele-specific nucleotide, 3' perfect match nucleotides and 5' perfect match nucleotides; wherein the allele-specific nucleotide is derived from known single nucleotide polymorphic site;
(b) performing a polymerase chain reaction with an universal primer set which anneals to both alleles to obtain a total molecule number;
(c) performing the polymerase chain reaction with an allele-specific primer and one of the universal primers to obtain the molecule number of one allele; and
(d) calculating an expression frequency of one allele by molecular number of one allele/total molecular number.

In a preferred embodiment, the polymerase chain reaction is performed by SYBR Green based quantitative PCR (qPCR) or TaqMan based real time PCR.

The method of the present invention can be applied to microRNA detection, gene expression, disease grading, cancer diagnosis or single nucleotide polymorphism.

The present invention further provides a quantitative method for assaying the expression ratio between alleles differed by a single nucleotide polymorphism which comprises:
(a) designing an allele-specific primer, according to nucleotide sequence of one species, which has, in 3' to 5' order, a 3'-hydroxyl allele-specific nucleotide, 3' perfect match nucleotides, at least one destabilizing mismatch nucleotide and 5' perfect match nucleotides, wherein the destabilizing mismatch nucleotide is selected from the group consisting of 3, 4, 5, 6 and 7 nucleotides upstream from the 3'-hydroxyl allele-specific nucleotide and is created by introducing transition or transversion substitution; and wherein the allele-specific nucleotide is derived from known single nucleotide polymorphic site;
(b) performing a polymerase chain reaction with an universal primer set which anneals to both alleles to obtain a total molecule number;
(c) performing the polymerase chain reaction with an allele-specific primer and one of the universal primers to obtain the molecule number of one allele; and
(d) calculating an expression frequency of one allele by molecular number of one allele/total molecular number.

In a preferred embodiment, the destabilizing mismatch nucleotide is selected from the group consisting of 3, 4, 5, 6 and 7 nucleotides upstream from the 3'-hydroxyl allele-specific nucleotide.

In a more preferred embodiment, the destabilizing mismatch nucleotide is selected from the group consisting of 4, 5 and 6 nucleotides upstream from the 3'-hydroxyl allele-specific nucleotide.

Preferably, the primer has two destabilizing mismatch nucleotides. More preferably, the primer has one destabilizing mismatch nucleotide.

In a preferred embodiment, the polymerase chain reaction is performed by SYBR Green based quantitative PCR (qPCR) or TagMan based real time PCR.

The method of the present invention can be applied to microRNA detection, gene expression, disease grading, cancer diagnosis or single nucleotide polymorphism.

The examples below are non-limiting and are merely representative of various aspects and features of the present invention.

EXAMPLES

Example 1

Materials and Methods

Preparation and Amplification of cDNA Templates for Quantitative Analysis

Times of development were expressed as hour postfertilization (hpf) and day postfertilization (dfp) at 28.5° C. Zebrafish embryos (*Danio rerio*) were collected 15-min after the beginning of the light cycle and defined as 0 hpf. Total RNA, treated with DNaseI, was extracted by the RNeasy kit (Qiagen). RNA (1-5 µg) was reverse transcribed by SuperScript III reverse transcriptase (Invitrogene) using oligo-d(T) and random hexamer as primers. A 20 µl reaction mixture contained 1 µl cDNA, 20 pmol primers, 200 µM each of the four dNTPs, 50 mM KCl, 10 mM Tris-HCl (pH 8.3), 1.5 mM MgCl$_2$ and 0.5 U of high fidelity KOD-plus DNA polymerase (Toyobo). The reagents and volume were reduced to half when purification of RT-PCR amplicon was not required. Reactions were run for 35 cycles (10 sec at 94° C., 20 sec at 55-60° C. and 1 min at 68° C.) and followed by a 10-min extension at 68° C.

Primers A1 (SEQ ID NO 1: 5'-GGAATGGCATGGTTG-GAGAACTGG-3') and A2 (SEQ ID NO 2: 5'-ACACCAC-CAACTATACGGCCAGACAA-3'), respectively derived from the sense and antisense sequences of exons 10 and 12, were used for amplifying gria2α mRNA (W.-H. Lin, Wu, C.-H, Chen, Y-C. and Chow, W-Y, Embryonic expression of zebrafish AMPA receptor genes: zygotic gria2α expression initiates at the midblastula transition. Brain Res. 1110 (2006) 46-54). Complementary DNA containing the Y/C site of zebrafish kainite receptor subunit, grik2α, was amplified by primers K1 (SEQ ID NO 3: 5'-AGCTGATCTTGCAGTG-GCGC-3') and K2 (SEQ ID NO 4: 5'-GGCCGTGTAGGAG-GAGATGATG-3'). PCR amplicons were separated by 2% agarose gel electrophoresis and purified by Geneclean (Bio101). Alternatively, PCR amplicons were separated by electrophoresis in a 2% low melting point agarose (SeaPlaque, BioWhittaker Molecular Applications), excised, washed and used without further purification for the qPCR analysis. RT-PCR amplicons were diluted before qPCR analysis. The RNA editing frequencies determined from the purified amplicons and amplicons in the excised gel yielded similar results, differed by less than 2% (data not shown).

Cloning and Preparation of Control DNA Templates

PCR amplicons were cloned to pGEMTeasy (Promega) and sequenced by the Bigdye terminator system (Applied Biosystems) to identify the A and G variants of gria2α and grik2α. Plasmids of edited (G) and unedited (A) variants were linearized with appropriated restriction enzymes, and cleaned by phenol/chloroform treatment. DNA concentrations were determined by spectrophotometry.

Quantitative PCR Assay

The Quantitative PCR (qPCR) was performed using SYBR Green Master Mix by following the manufacturer's suggestions (Applied Biosystems). Primer pairs were designed with the aid of PrimerExpress (Applied Biosystems), the melting temperature was set at 60° C. and the length of the amplicon was kept between 80-100 bp. Sequences of real-time PCR primers are listed in Table 1. Reactions contained 800 fmol of each primer in a total volume of 10 µl. The Ct values, as defined by the default setting, were measured by ABI PRISM 7500™ Sequence Detection System. After an initial 2 min at 50° C. and 10 min at 95° C., the thermal profile consisted of 45 cycles of 10 s at 95° C. and 1 min at 60° C. Nevertheless, reactions usually reached plateau stage before the 30$^{th}$ cycle, a 35-cycle reaction was sufficient. Single-product amplification was confirmed by post-reaction dissociation analysis. Duplicate samples were measured and averaged. If duplicates differed by more than 0.3 Ct value, the sample was remeasured.

TABLE 1

Sequences of real-time PCR primers used in the invention

| Primer | Sequence (5'-3')[a] | Purpose[b] |
|---|---|---|
| AU3 | TCTTCCTCGTTAGCCGCTTC | Forward universal primer for gria2α |
| AU4 | CAAAGACCTTGGCGAAATATCG | Reverse universal primer for gria2α |
| A2Q1 | CGAAATATCGCATCCCTGC | Reverse primer for unedited form of gria2α |
| KU3 | TCCAAACCCTTCATGACGCT | Forward universal primer for grik2α |
| KU4 | CAGCACACAACTGACACCCAA | Reverse universal primer for grik2α |
| K2Y1 | GCACACAACTGACACCCAAG | Reverse primer for unedited form of grik2α |
| K2Y2 | CAGCACACAACTGACAC<u>T</u>CAAG | Reverse primer for unedited form of grik2α |
| K2Y3 | CAGCACACAACTGACAC<u>TT</u>AAG | Reverse primer for unedited form of grik2α |
| K2Y4 | CAGCACACAACTGACACC<u>T</u>AAG | Reverse primer for unedited form of grik2α |

[a]The positions of mismatched bases are underlined. The position of a single base variation is highlighted in gray.
[b]Relative positions of primers are depicted in FIG. 1B.

Measurement of RNA Editing Frequency by qPCR

The amplification efficiency (standard curve) of each primer pair was established by measuring the Ct values of series dilutions of the linearized plasmid DNA templates. In simulation experiments, the amounts of the A and G variant DNAs were separately determined by the universal primers. Known amounts (expected molecule numbers) of A and G variants were then mixed in various ratios and used for qPCR analysis. To determine the RNA editing frequency, the amount of RT-PCR product was pre-determined by the universal primer so that approximately 1 pg of RT-PCR amplicon, which would give rise to a Ct value around 17, was used in each qPCR analysis. Equal amount of RT-PCR amplicon was quantified by the A-specific primer pair and by the universal primer pair. The molecule numbers of the A variant and the total (A and G variants) molecule were then calculated by fitting Ct values to the equations derived from standard curves. The equations were log [molecule number of gria2α (A)]=−0.314Ct+10.74, log [molecule number of gria2α]=−0.3005Ct+10.655, log [molecule number of grik2α(A)]=−0.297Ct+15.72407, and log [molecule number of grik2α]=−0.30178Ct+15.724. The RNA editing frequency was calculated as 1-(molecule number of A variant/total molecule number).

Example 2

Establishment of the Quantitative PCR Measurement of RNA Editing Frequencies

As illustrated in FIG. 1, the steps involved in the determination of RNA editing frequency at a specific site by qPCR. Transcripts with the edited sites were amplified by RT-PCR. The RT-PCR amplicons were mixtures of A (unedited) and G (edited) variants. Agarose bands containing the RT-PCR amplicons were excised after gel electrophoresis (FIG. 1A). The amount of RT-PCR amplicon was quantified by the universal primer pair annealing to both the A and G variants, and the amount of A variant in the RT-PCR amplicon was quantified by the forward universal primer and the A-specific reverse primer (FIG. 1B). The 3' ends of A-specific primers were placed at the editing site to differentially amplify (quantify) the A and G variants (FIG. 1B and Table 1).

Figure 2:
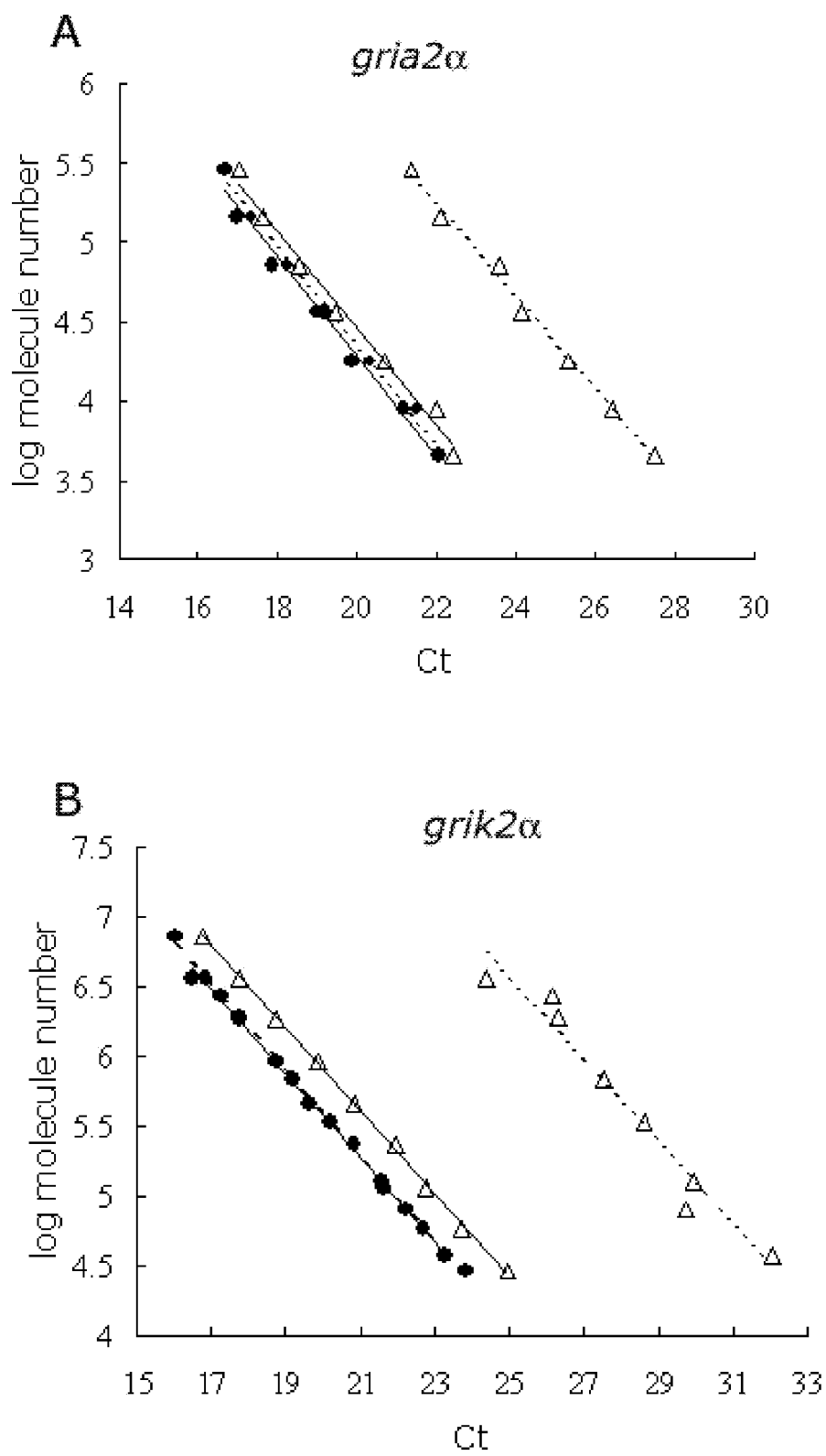
FIG. 2 shows amplification efficiencies of the A-specific and universal primer pairs. A. The standard curves established on the gria2α templates. B. the standard curves established on the grik2α templates. Solid and dashed lines respectively represent the amplification efficiencies of A and G variant templates by the A-specific (open triangles) and by the universal primer pairs (filled circles).

Conditions and primers for measuring the RNA editing frequencies at the Q/R site of zebrafish gria2α and at the Y/C site of grik2α were established. To evaluate the performances of qPCR primer pairs, the amplification efficiencies of A-specific primer pair (AU3-A2Q1) and universal primer pair (AU3-AU4) on the A variant and G variant of gria2α templates were compared (FIG. 2A). The universal and A-specific primer pairs displayed similar amplification efficiencies on the perfectly matched gria2α templates, whereas the A-specific primer pair (AU3-A2Q1) displayed a 32-fold (ΔCt=−5) higher efficiency on the perfectly-matched A variant (unedited Q-form) than that on the mismatched G variant (edited R-form, FIG. 2A).

On the other hand, the A-specific primer pair (KU3-K2Y1) amplified A (unedited Y-form) and G (edited C-form) variants of grik2α with similar efficiencies, indicating that the K2Y1 primer with only one mismatch at the 3' end could not discriminate the Y/C editing variants of grik2α (data not shown). Internal mismatches were introduced into the A-specific primer (K2Y2, K2Y3 and K2Y4, Table 1). K2Y2, K2Y3 and K2Y4 contain 1 or 2 nucleotide internal destabilizing mismatches 3-5 nucleotides upstream from the 3' end. The abilities of these primers to differentially amplify the A and G variants of grik2α were tested on two concentrations of templates (Table 2). The A variant was more efficiently amplified than the G variant of grik2α by the A-specific primers with internal mismatches. However, relative to the amplification efficiency of the universal primer (KU4), the amplification efficiencies of primers with internal mismatches on the A variant reduced 1 to 12-fold (Table 2). The standard curves established by the universal primer pair (KU3-KU4) and the A-specific primer pair (KU3-K2Y4) confirmed that the primer K2Y4 with an internal mismatched nucleotide could distinguish between the A and G variants of grik2α (FIG. 2B).

TABLE 2

Effects of internal mismatches on the amplification of A and G variants of the grik2α Y/C site

|  | KU4 | K2Y2 | K2Y3 | K2Y4 |
|---|---|---|---|---|
| A variant (high) | 15.12 | 17.95 | 17.94 | 16.30 |
| G variant (high) | 15.16 | 20.54 | 30.09 | 22.87 |
| A variant (low) | 19.81 | 20.29 | 23.44 | 20.47 |
| G variant (low) | 19.82 | 25.76 | 36.87 | 28.13 |

Note.
Figures in the table are Ct values.
[a]The amount of high-concentration DNA is approximately 50-fold greater than that of low-concentration DNA.

Figure 3:
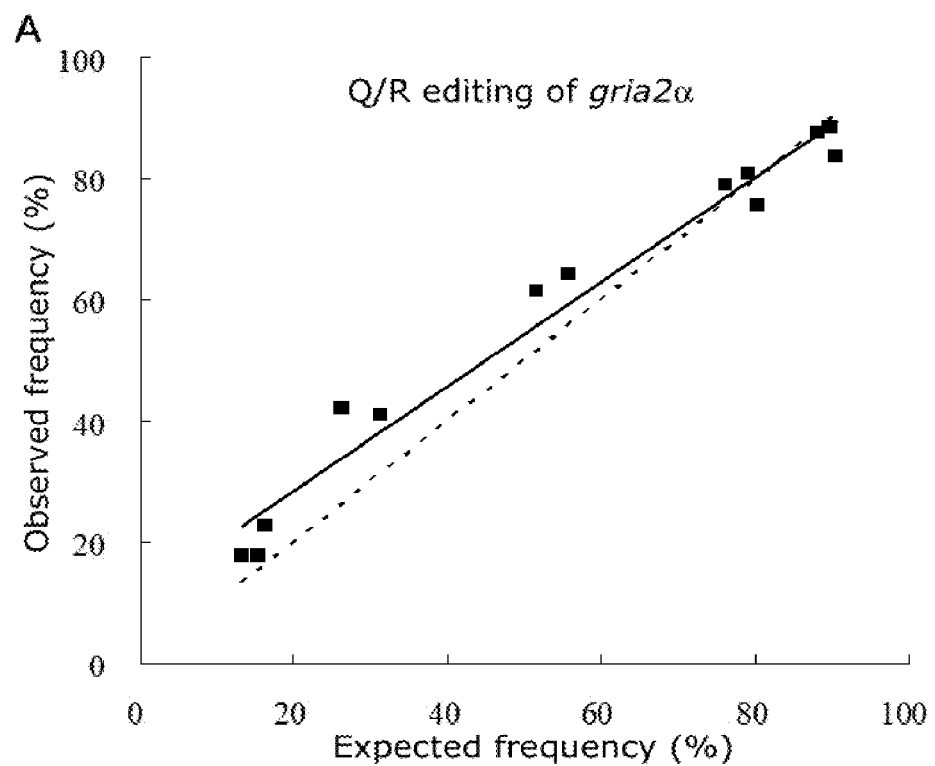
FIG. 3 shows correlations between the expected and observed RNA editing frequencies. RNA editing frequencies were calculated from the results of qPCR analysis (observed frequency) and were plotted against the known ratios of G and A variants (expected frequency). Solid lines show the linear relationship between the expected and observed RNA editing frequencies. Dashed lines project the expected linear relationship.
Figure 3:
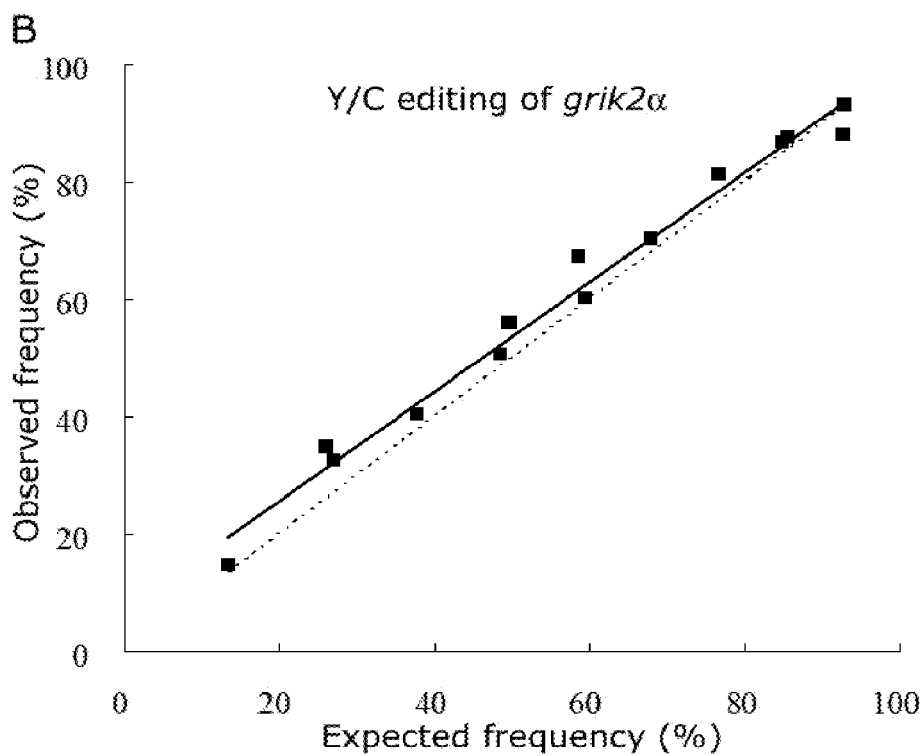

The performance of the A-specific primer was also evaluated on mixed templates with various ratios between A and G variants. The estimated (observed) proportions of A variant were converted to editing frequencies (1—molecule number of A variant/total molecule number) and plotted against the actual proportions of G variant in the mixed DNAs. The observed and expected frequencies displayed an expected linear relationship ($r > 0.98$, FIG. 3). These results demonstrated that allele-specific primers, with and without internal destabilizing mismatch nucleotide, could be designed for reliable distinction transcripts from two alleles with single-nucleotide difference to determine the expression frequency of a given transcript.

Reproducibility of qPCR Analysis

The reproducibility of qPCR method was tested by measuring 6 independent RT-PCR amplifications using the same total RNA. The mean editing frequency of grik2α mRNA extracted from the 24 hpf embryo was 40.9% with a standard deviation (S.D.) of 1.0%, and editing frequency of gria2α mRNA extracted from the 4 hpf embryo was 62.3±3.2% (mean±S.D.). The Q/R RNA editing frequency measured from gria2α mRNA extracted the 24 hpf embryo were 91.2±0.8% (n=3). These results demonstrated that the qPCR method is highly reproducible.

Example 3

Comparison of RNA Editing Frequencies Determined by the qPCR and by Primer Extension Methods Limited primer extension was performed as previously described by Lin et al. (W.-H. Lin, Wu, C.-H, Chen, Y.-C. and Chow, W.-Y., Embryonic expression of zebrafish AMPA receptor genes: zygotic gria2α expression initiates at the mid-blastula transition. Brain Res. 1110 (2006) 46-54) to measure the frequency of Q/R editing of gria2α. Briefly, a primer extension reaction contained 10 pmol of the $^{33}$P-end-labeled oligonucleotide, 100 ng of gel-purified gria2α PCR amplicon, 0.3 U of the Klenow enzyme (Roche), 1 mM dideoxy-GTP and 0.1 mM each of dTTP, dCTP and dATP. The products extended from the edited and unedited variants, differed by 1 nt-long, were resolved by 8 M urea/20% PAGE. Intensities of both extension products, edited and unedited, were quantified after autoradiography and calculated by UN-SCAN-IT Gel™ Version 5.1 software. Alternatively, the gel-purified RT-PCR amplicons of grik2α were sequenced by the Bigdye terminator system (Applied Biosystems) with an internal primer (SEQ ID NO 3: 5' AGCTGATCTTGCAGTG-GCGC 3') to estimate the RNA editing frequency at the Y/C site.

Figure 4:
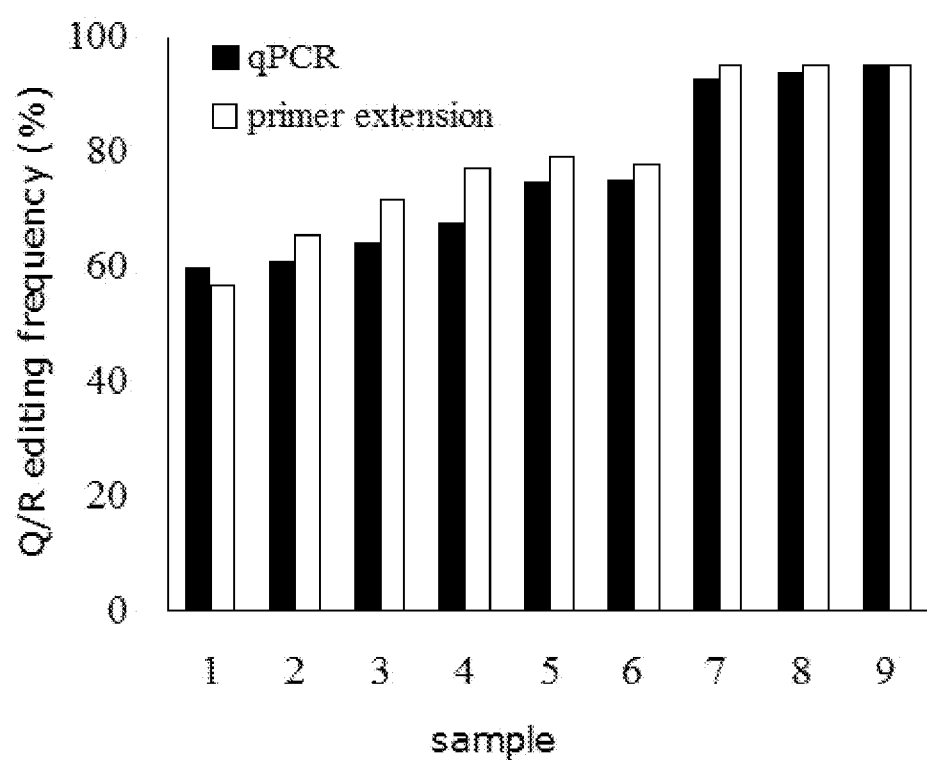
FIG. 4 shows comparison of RNA editing frequencies determined by the qPCR and limited primer extension analyses. Solid and open bars respectively indicate the RNA editing frequencies at the Q/R site of gria2α determined by the qPCR and primer extension methods.

The RNA editing frequencies of nine gria2α amplicons, amplified from embryonic RNA samples, determined by the qPCR and primer extension analyses were compared (FIG. 4). In general, the RNA editing frequencies measured by the primer extension were slightly higher than those measured by the qPCR method. The average difference between the RNA editing frequencies determined by the two methods was 3.7%. The differences were less than 2% when the editing frequency was higher than 90% (samples 7-9, FIG. 4). A higher average difference (4.86%, n=6) was observed when Q/R editing frequencies were between 62 to 75% (samples 1-6, FIG. 4). The correlation coefficiency was 0.96 between the RNA editing frequencies measured by the two methods. Most importantly, the rank orders of RNA editing efficiency were similar between the two methods (FIG. 4), demonstrating that the qPCR method could as reliably analyze the changes of RNA editing activity as the primer extension method.

Figure 5:
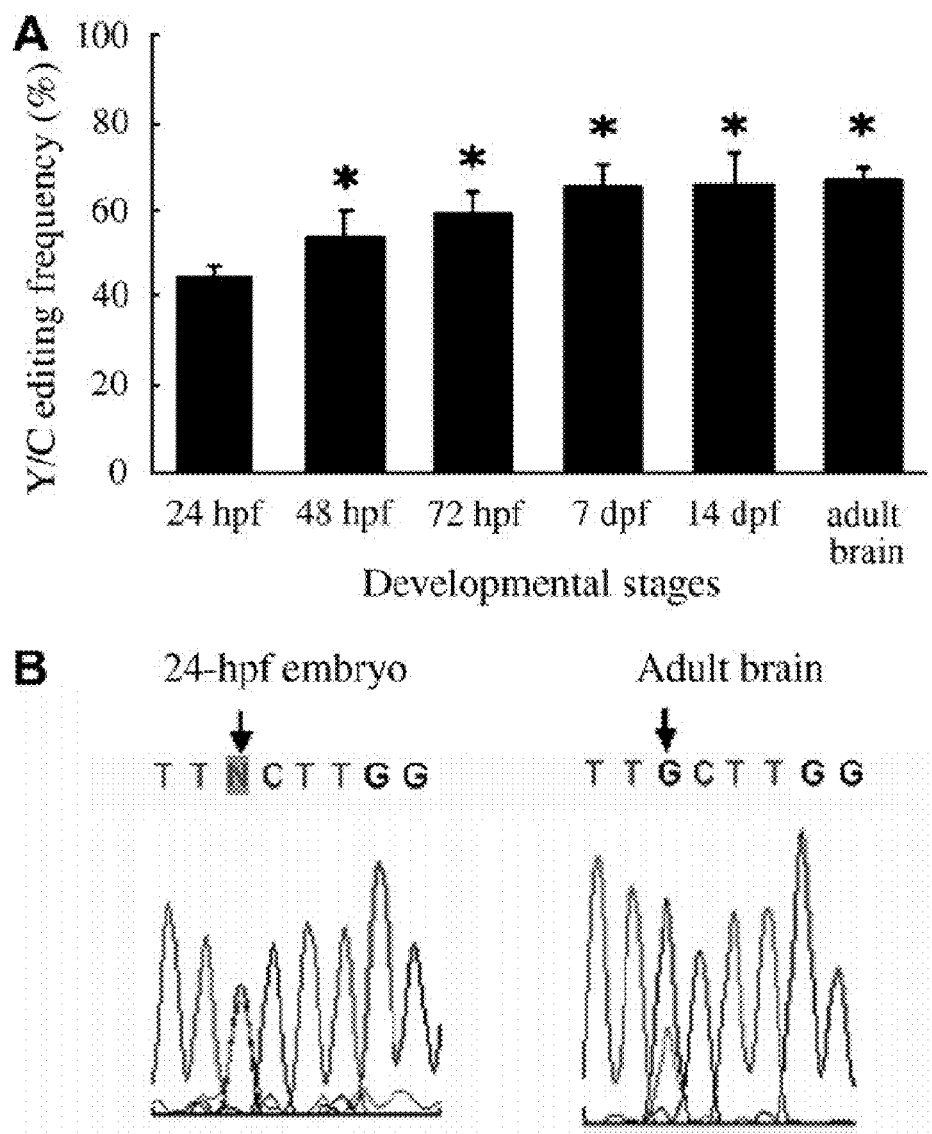
FIG. 5 illustrates Y/C RNA editing of grik2α during zebrafish development. (A) Frequencies of Y/C editing determined by the qPCR analysis. Values represented mean±standard deviation. Except for the 72 hpf and adult brain (n=3), more than 5 embryo populations were measured at the other stages. Developmental stages were expressed as hpf (hour postfertilization) and dpf (day postfertilization). Statistic analysis was performed by the Student's t-test.

Application of qPCR Using Internal Destabilizing Mismatch Primer in the Measuring Y/C Editing Frequency in Biological Samples The qPCR method was applied to assay the RNA editing of grik2α at Y/C site during zebrafish development (FIG. 5A). Approximately 44.6% of the grik2α mRNA were edited (C on the Y/C site) at 24 hpf, and the editing at the Y/C site increased significantly between 24 to 48 hpf. The level of Y/C editing was 54.4±5.45% (n=5) at 48 hpf and remained relatively stable at later developmental stages. The grik2α amplicons were also analyzed by direct sequence analysis. Two representative chromatograms are shown in the FIG. 5B. Consistent to the results obtained by the qPCR analysis, the ratios between the G and A peaks were higher in amplicons derived from the brain than amplicons derived from the 24-hpf embryos (FIG. 5B).

While the invention has been described and exemplified in sufficient detail for those skilled in this art to make and use it, various alternatives, modifications, and improvements should be apparent without departing from the spirit and scope of the invention.

One skilled in the art readily appreciates that the present invention is well adapted to carry out the objects, and attain the aims and advantages mentioned, as well as those inherent therein. Modifications therein and other uses will occur to those skilled in the art. These modifications are encompassed within the spirit of the invention and are defined by the scope of the claims.

What is claimed is:

1. A quantitative method for assaying the expression ratio between alleles differed by a single nucleotide polymorphism which comprises:
   (a) designing an allele-specific primer, according to nucleotide sequence of one allele, which has, in 3' to 5' order, a 3'-hydroxyl allele-specific nucleotide, 3' perfect match nucleotides and 5' perfect match nucleotides; wherein the allele-specific nucleotide is derived from known single nucleotide polymorphic site;
   (b) performing a polymerase chain reaction with an universal primer set which anneals to both alleles to obtain a total molecule number;
   (c) performing the polymerase chain reaction with an allele-specific primer and one of the universal primers to obtain the molecule number of one allele; and
   (d) calculating an expression frequency of one allele by molecular number of one allele/total molecular number.

2. The method of claim 1, wherein the polymerase chain reaction is performed by SYBR Green based quantitative PCR or TaqMan based real time PCR.

3. The method of claim 1, which is applied to microRNA detection, gene expression, disease grading, cancer diagnosis or single nucleotide polymorphism.

4. A quantitative method for assaying the expression ratio between alleles differed by a single nucleotide polymorphism which comprises:
   (a) designing an allele-specific primer, according to nucleotide sequence of one species, which has, in 3' to 5' order, a 3'-hydroxyl allele-specific nucleotide, 3' perfect match nucleotides, at least one destabilizing mismatch nucleotide and 5' perfect match nucleotides, wherein the destabilizing mismatch nucleotide is selected from the group consisting of 3, 4, 5, 6 and 7 nucleotides upstream from the 3'-hydroxyl allele-specific nucleotide and is created by introducing transition or transversion substitution; and wherein the allele-specific nucleotide is derived from known single nucleotide polymorphic site;
   (b) performing a polymerase chain reaction with an universal primer set which anneals to both alleles to obtain a total molecule number;

(c) performing the polymerase chain reaction with an allele-specific primer and one of the universal primers to obtain the molecule number of one allele; and (d) calculating an expression frequency of one allele by molecular number of one allele/total molecular number.

5. The method of claim 4, wherein the destabilizing mismatch nucleotide is selected from the group consisting of 4, 5 and 6 nucleotides upstream from the 3'-hydroxyl allele-specific nucleotide.

6. The method of claim 4, wherein the primer has two destabilizing mismatch nucleotides.

7. The method of claim 6, wherein the primer has one destabilizing mismatch nucleotide.

8. The method of claim 4, wherein the polymerase chain reaction is performed by SYBR Green based quantitative PCR (qPCR) or TagMan based real time PCR.

9. The method of claim 4, which is applied to microRNA detection, gene expression, disease grading, cancer diagnosis or single nucleotide polymorphism.

* * * * *

```
                        SEQUENCE LISTING

<160> NUMBER OF SEQ ID NOS: 13

<210> SEQ ID NO 1
<211> LENGTH: 24
<212> TYPE: DNA
<213> ORGANISM: Danio rerio
<220> FEATURE:
<221> NAME/KEY: primer_bind
<222> LOCATION: (1)..(24)

<400> SEQUENCE: 1
ggaatggcat ggttggagaa ctgg                                          24

<210> SEQ ID NO 2
<211> LENGTH: 26
<212> TYPE: DNA
<213> ORGANISM: Danio rerio
<220> FEATURE:
<221> NAME/KEY: primer_bind
<222> LOCATION: (1)..(26)

<400> SEQUENCE: 2
acaccaccaa ctatacggcc agacaa                                        26

<210> SEQ ID NO 3
<211> LENGTH: 20
<212> TYPE: DNA
<213> ORGANISM: Danio rerio
<220> FEATURE:
<221> NAME/KEY: primer_bind
<222> LOCATION: (1)..(20)

<400> SEQUENCE: 3
agctgatctt gcagtggcgc                                               20

<210> SEQ ID NO 4
<211> LENGTH: 22
<212> TYPE: DNA
<213> ORGANISM: Danio rerio
<220> FEATURE:
<221> NAME/KEY: primer_bind
```

```
<222> LOCATION: (1)..(22)

<400> SEQUENCE: 4
ggccgtgtag gaggagatga tg                                              22

<210> SEQ ID NO 5
<211> LENGTH: 20
<212> TYPE: DNA
<213> ORGANISM: Danio rerio
<220> FEATURE:
<221> NAME/KEY: primer_bind
<222> LOCATION: (1)..(20)

<400> SEQUENCE: 5
tcttcctcgt tagccgcttc                                                 20

<210> SEQ ID NO 6
<211> LENGTH: 22
<212> TYPE: DNA
<213> ORGANISM: Danio rerio
<220> FEATURE:
<221> NAME/KEY: primer_bind
<222> LOCATION: (1)..(22)

<400> SEQUENCE: 6
caaagacctt ggcgaaatat cg                                              22

<210> SEQ ID NO 7
<211> LENGTH: 20
<212> TYPE: DNA
<213> ORGANISM: Danio rerio
<220> FEATURE:
<221> NAME/KEY: primer_bind
<222> LOCATION: (1)..(20)

<400> SEQUENCE: 7
cgaaatatcg catccctgct                                                 20

<210> SEQ ID NO 8
<211> LENGTH: 20
<212> TYPE: DNA
<213> ORGANISM: Danio rerio
<220> FEATURE:
<221> NAME/KEY: primer_bind
<222> LOCATION: (1)..(20)

<400> SEQUENCE: 8
tccaaaccct tcatgacgct                                                 20

<210> SEQ ID NO 9
<211> LENGTH: 21
<212> TYPE: DNA
<213> ORGANISM: Danio rerio
<220> FEATURE:
<221> NAME/KEY: primer_bind
<222> LOCATION: (1)..(21)

<400> SEQUENCE: 9
cagcacacaa ctgacaccca a                                               21

<210> SEQ ID NO 10
<211> LENGTH: 21
<212> TYPE: DNA
<213> ORGANISM: Danio rerio
<220> FEATURE:
<221> NAME/KEY: primer_bind
<222> LOCATION: (1)..(21)
```

-continued

```
<400> SEQUENCE: 10
gcacacaact gacacccaag t                                              21

<210> SEQ ID NO 11
<211> LENGTH: 23
<212> TYPE: DNA
<213> ORGANISM: Artificial
<220> FEATURE:
<223> OTHER INFORMATION: modified from Danio rerio
<220> FEATURE:
<221> NAME/KEY: primer_bind
<222> LOCATION: (1)..(23)

<400> SEQUENCE: 11
cagcacacaa ctgacactca agt                                            23

<210> SEQ ID NO 12
<211> LENGTH: 23
<212> TYPE: DNA
<213> ORGANISM: Artificial sequence
<220> FEATURE:
<223> OTHER INFORMATION: modified from Danio rerio
<220> FEATURE:
<221> NAME/KEY: primer_bind
<222> LOCATION: (1)..(23)

<400> SEQUENCE: 12
cagcacacaa ctgacactta agt                                            23

<210> SEQ ID NO 13
<211> LENGTH: 23
<212> TYPE: DNA
<213> ORGANISM: Artificial sequence
<220> FEATURE:
<223> OTHER INFORMATION: modified from Danio rerior
<220> FEATURE:
<221> NAME/KEY: primer_bind
<222> LOCATION: (1)..(23)

<400> SEQUENCE: 13
cagcacacaa ctgacaccta agt                                            23
```